United States Patent [19]
Sutherland

[11] Patent Number: 5,129,909
[45] Date of Patent: Jul. 14, 1992

[54] APPARATUS AND METHOD FOR MAKING PRECISE BONE CUTS IN TOTAL KNEE REPLACEMENT

[76] Inventor: Charles J. Sutherland, 232 N. Kingshighway, No. 2401, St. Louis, Mo. 63108

[21] Appl. No.: 668,887

[22] Filed: Mar. 13, 1991

[51] Int. Cl.⁵ .................................................. A61H 2/00
[52] U.S. Cl. ........................................ 606/88; 606/86; 606/53
[58] Field of Search .................. 606/53, 79, 82, 86, 606/87, 88, 96

[56] References Cited
U.S. PATENT DOCUMENTS

| | | | |
|---|---|---|---|
| 4,421,112 | 12/1983 | Mains et al. | 606/96 X |
| 4,567,885 | 2/1986 | Androphy | 606/88 |
| 4,718,413 | 1/1988 | Johnson | 606/82 |
| 4,759,350 | 7/1988 | Dunn et al. | 606/82 |
| 4,791,919 | 12/1988 | Elloy et al. | 606/82 X |
| 4,892,093 | 1/1990 | Zarnowski et al. | 606/82 |
| 4,926,847 | 5/1990 | Luckman | 606/88 |
| 5,042,983 | 8/1991 | Rayhack | 606/53 X |

FOREIGN PATENT DOCUMENTS 0243109 10/1987 European Pat. Off. ............ 606/82

Primary Examiner—Robert A. Hafer
Assistant Examiner—Sam Rimell
Attorney, Agent, or Firm—Flehr, Hohbach, Test, Albritton & Herbert

[57] ABSTRACT

Apparatus for making a precise cut in a bone comprising a cutting block having at least one saw-guiding slot therein. A screw is carried by the block and is adapted to secure the block to the bone so that the block is held in compression against the bone.

3 Claims, 2 Drawing Sheets

APPARATUS AND METHOD FOR MAKING PRECISE BONE CUTS IN TOTAL KNEE REPLACEMENT

This invention relates to an apparatus and method for making precise bone cuts, and more particularly to an apparatus and method for making precise bone cuts in a total knee replacement.

Total knee replacements in humans have been undertaken for a number of years. Johnson & Johnson has provided a P.F.C. ® Modular Knee System with SPECIALIST ® Instruments for performing such total knee replacements Implantation of press-fit, noncemented total knee components such as utilized in the P.F.C. Modular Knee System requires very precise bone cuts (osteotomy). In the past, such bone cuts have been made by an oscillating saw utilizing cutting blocks stabilized by pinning and clamping It has been found that such approaches have not provided adequate rigid fixation of the cutting block to the bone. This made it very difficult if not impossible to predictably achieve a press-fit of the femoral component on the distal femur. As is well known to those skilled in the art, a press fit or exact fit is required for successful bone-ingrowth fixation of joint replacement components. There is therefore a need for a new and improved apparatus and method to overcome these deficiencies.

In general, it is an object of the present invention to provide an apparatus and method for making precise bone cuts in total knee replacements.

Another object of the invention is to provide an apparatus and method of the above character in which a cutting block is used which is rigidly secured to the bone on which the cuts are to be made.

Another object of the invention is to provide an apparatus and method of the above character in which the cutting block is compressed against the bone to achieve absolute stability of the cutting block during the precision cutting operations.

Another object of the invention is to provide an apparatus and method of the above character which does not damage the bone or soft tissues.

Another object of the invention is to provide an apparatus and method of the above character in which precision cuts can be made quickly and without complicated equipment.

Additional objects and features of the invention will appear from the following descriptions in which the preferred embodiments are set forth in detail in conjunction with the accompanying drawings.

FIG. 1 is a top plan view of the apparatus of the present invention and particularly showing a cutting block mounted axially of the femur of a human being.

FIG. 2 a cross sectional view taken along the line 2—2 of FIG. 1.

Figure 1:
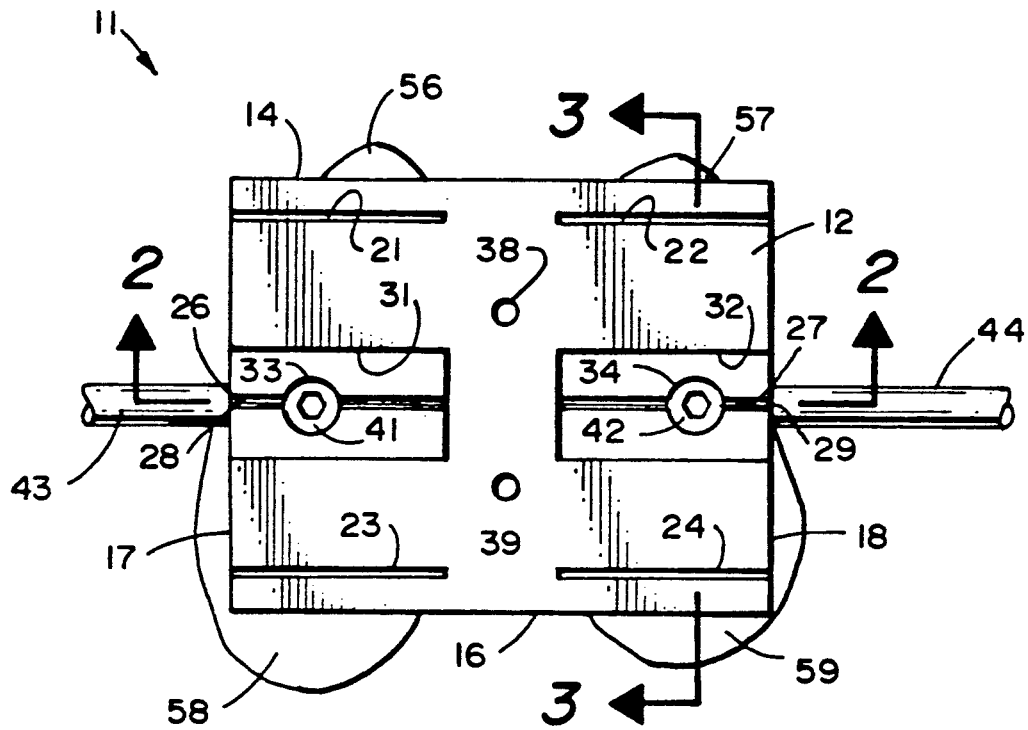

In general, the apparatus of the present invention for making a precise cut in a bone is comprised of a cutting block having at least one saw-guiding slot formed therein. Means is provided on the block for securing the block to the bone so that the block is held in compression against the bone. Compression is achieved by the use of at least one lag screw securing the block to the bone.

The method for making precise bone cuts is accomplished by the use of a cutting block having at least one saw-guiding slot therein Planar surfaces are formed on the bone which lies in a predetermined plane. The block is secured to the planar surface of the bone so that the cutting block is compressed against the bone. At least one precise cut is then made by introducing a saw blade through the saw-guiding slot while the block is held in compression against the bone. After the desired number of precise cuts have been made utilizing the cutting block, the cutting block is removed. The prosthesis is then placed on the bone over the bone cuts and in contact therewith.

More particularly, the apparatus for making precise bone cuts consists of a cutting block 11 which is formed of a suitable surgical metallic alloy. The block 11 is in the form of a solid parallelpiped having top and bottom surfaces 12 and 13, sidewalls 14 and 16 and end walls 17 and 18.

The cutting block 11 is provided with at least one saw-guiding slot. Thus, as shown in the drawings, the block 11 is provided with first and second spaced apart anterior guiding slots 21 and 22 which are in alignment with each other and extend approximately perpendicular to the top surface 12 and the bottom surface 13. Slots 21 and 22 may open through the end walls 17 and 18 and are spaced an adequate distance from the side wall 14. To prevent mechanical distortion of the cutting block during the operation of the saw blade in the slot, posterior guiding slots 23 and 24 are similarly provided in the block 11. These slots 23 and 24 extend vertically through the surfaces 12 and 13 and may open through the end walls 17 and 18. They are also spaced from the sidewall 16 by approximately the same distance that the slots 21 and 22 are spaced from the sidewall 14.

Aligned inclined spaced apart medial and lateral anterior chamfer-guiding slots 26 and 27 are provided which are spaced inwardly from the anterior guide slots 21 and 22. They extend through the bottom surface 13 and through the top surface 12. They are inclined at a suitable angle, as for example approximately 45° from the vertical. Aligned inclined spaced apart medial and lateral posterior chamber guiding slots 28 and 29 are provided which are spaced inwardly from the posterior guide slots 23 and 24. The slots 28 and 29 extend through the top and bottom surfaces 12 and 13 and through the end walls 17 and 18. The slots 28 and 29 are also inclined from the vertical by a suitable angle, as for example 45°.

Aligned spaced apart V-shaped upwardly facing recesses 31 and 32 are provided which extend through the surface 12 and the end walls 17 and 18 and are formed by intersection of the guide slots 26 and 27 and 28 and 29. Holes 33 and 34 are formed in the block 11 within the recesses 31 and 32 and are centrally disposed with respect to the slots 26 and 31 and the slots 27 and 32. The holes 33 and 34 extend downwardly through the V-shaped recesses 31 and 32 to a depth which is below the line through which the slots 26 and 29 and slots 27 and 29 intersect. Centrally disposed bores 36 and 37 are provided in the holes 33 and 34, and have a diameter which is less than the diameters of the holes 33 and 34. The bores 36 and 37 extend through the bottom wall 13.

The apparatus of the present invention includes means for securing the cutting block 11 to the bone in which the precision cut or cuts are to be made, and to hold the block in compression against the bone. This means consists of at least one and preferably two lag screws 41 and 42. The lag screws 41 and 42 are provided with heads 41a and 42a, as well as threaded portions 41b and 42b, respectively. The lag screws can be of a suitable type, as for example lag screws having a diameter of 6.5 millimeters and a length of 35 millimeters. The lag screws 41 and 42 are of a cancellous type which are adapted to be utilized with bone. The heads 41a and 42a are provided with screwdriver slots 46 of a conventional surgical type, as for example recessed hex-head slots.

Figure 3:
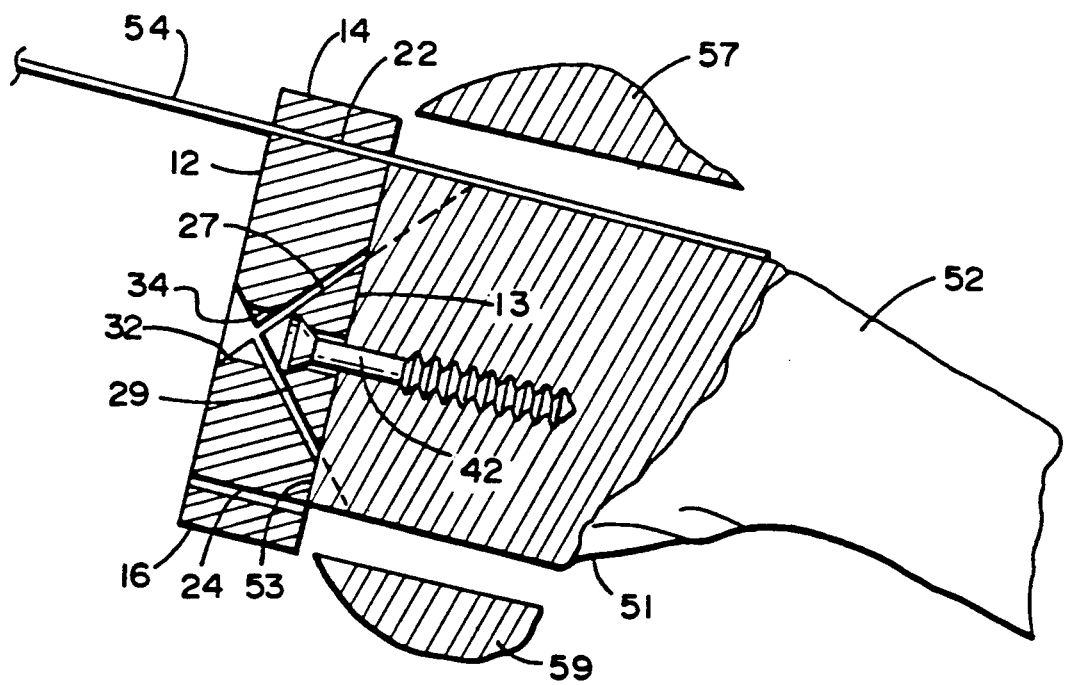
FIG. 3 is a cross sectional view taken along the line 3—3 of FIG. 1.
Figure 4:
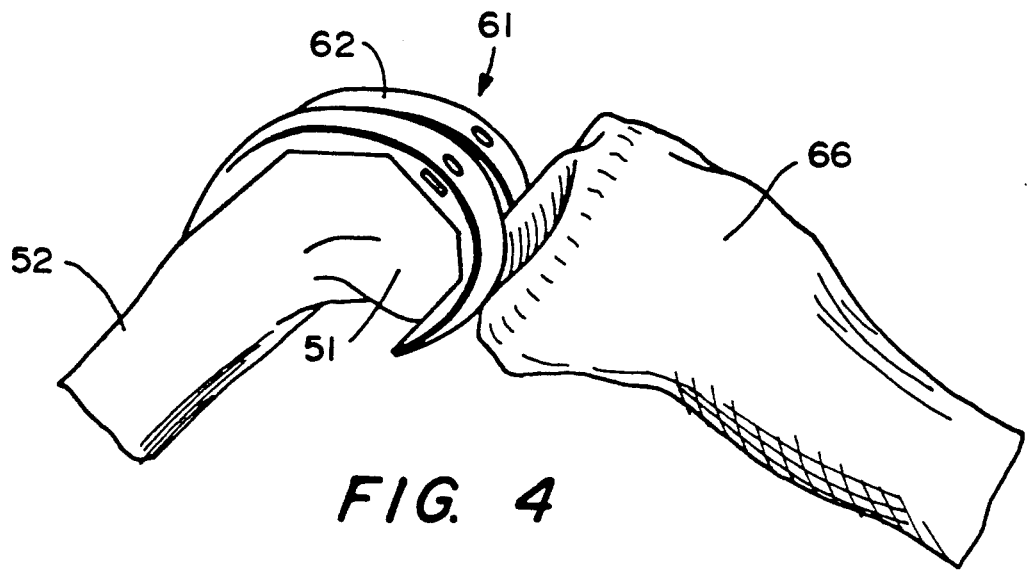
FIG. 4 is a perspective view showing the femoral trial in place on precise bone cuts that have been made in the femur.
Figure 2:
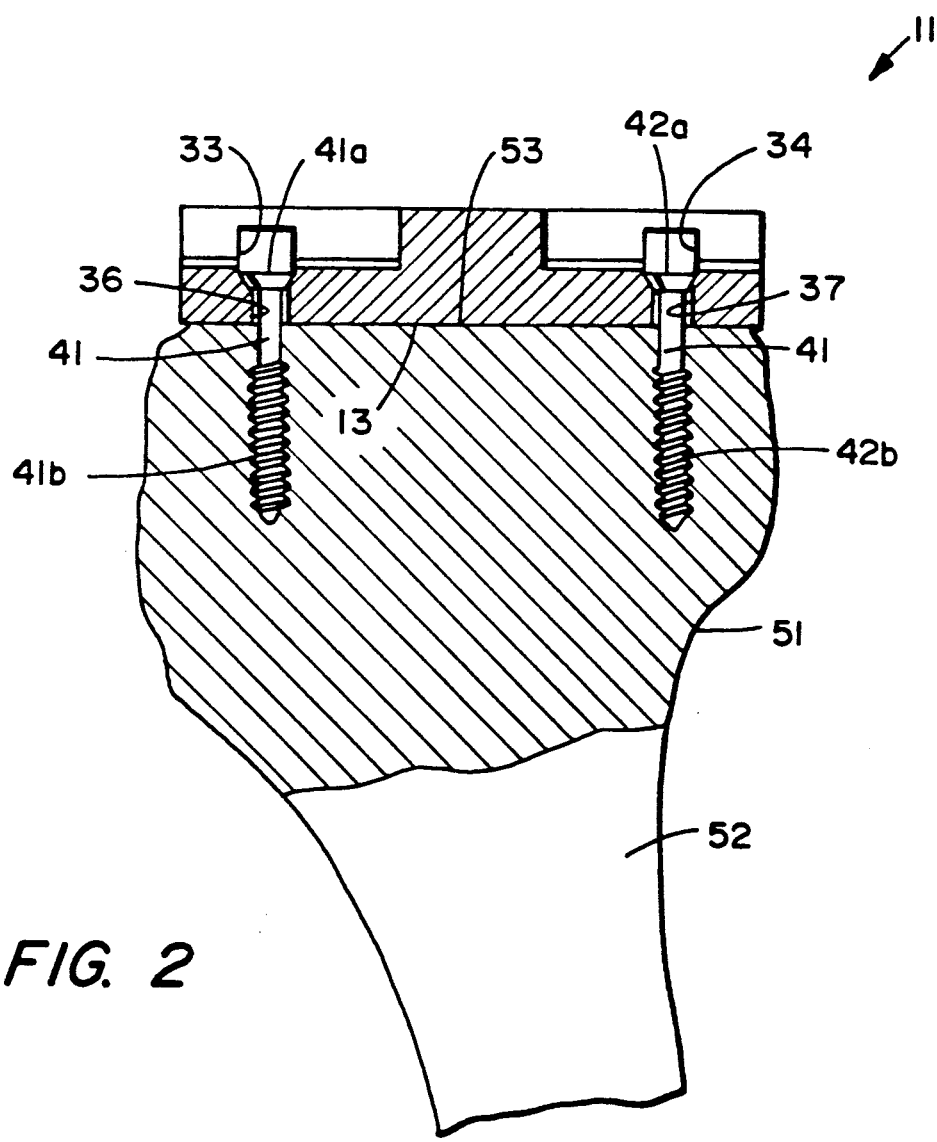

The use of the apparatus hereinbefore described in performing my method may now be briefly described as follows Let it be assumed that it is desired to utilize the P.F.C. ® Modular Knee System of Johnson & Johnson. Let is be assumed that in this procedure the distal extremity 51 of the femur 52 has been exposed A femoral cutting block (not shown) is positioned on the distal 51, and an oscillating saw (not shown) is used to accomplish a distal femoral resection by removal or resection of the distal condyles to provide planar surfaces 53 (see FIG. 3). This prevision osteotomy (bone cut) of the distal femur 51, producing a planar resection 53 of the distal femur, is carried out using an appropriate cutting block and lag screw(s) for rigid fixation of the cutting block in a manner analogous to the method described in detail below. Care should be taken that these surfaces 53 lie in a plane and are as flat as possible The segments of the distal condyles which are removed have dimensions equivalent to the distal dimension of the prosthesis which is to be utilized in connection with the knee replacement. The size of the prosthesis is estimated and a corresponding pin template (not shown) is selected and oriented on the cut distal femoral surfaces 53 in the proper position. A pin punch (not shown) is used to make two small holes in the distal femoral bone. Since this bone is cancellous, further drilling or tapping is unnecessary.

Thereafter, in accordance with the present invention, the cutting block 11 is positioned with its bottom surface on the surface 53 of the femur 52. With the holes 36 and 37 lined up with the two punched holes previously placed in the bone, the two 6.5 mm cancellous lag screws 41 and 42 are inserted in the holes 33 and 34 and extend through the bores 36 and 37. The lag screws 41 and 42 are driven into the punched holes previously provided by the use of a hand or power-driven screwdriver until the cutting block 11 is secured firmly in place on the surface 53 to provide a compression fit between the bottom surface 13 of the cutting block 11 and the top surface 53 of the femur 52. The screw heads 41b and 42b make it possible to readily achieve such compression fit, and serve to rigidly fix the cutting block 11 to the femur. Thereafter, precision osteotomies can be readily accomplished by use of a conventional oscillating saw (not shown) by introducing the saw blade into the guiding slots. Thus, for example, the oscillating saw blade 54 can be utilized to first remove the anterior femoral condyles 56 and 57 by extending the saw blade 54 through the vertically disposed slots 21 and 22. Thereafter, the posterior femoral condyles 58 and 59 can be removed in a similar manner by introducing the saw blade 54 into the guide slots 23 and 24, respectively. Thereafter, anterior chamfers can be formed on the distal extremity 51 of the femur 52 by introducing the saw blade 54 into the inclined slots 26 and 27. Similarly, posterior chamfers can be provided on the distal extremity 57 of the femur 52 by extending a saw blade 54 through the slots 31 and 32.

It has been found that by securing the cutting block 11 to the femur by the use of compression screws to provide a compression fit of the type hereinbefore described, that the cutting block does not move but remains in a fixed position with respect to the distal extremity 51 of the femur 52, making it possible to make precise bone cuts. After all of the bone cuts have been made, the screws 41 and 42 are removed by the use of a hand or power-driven screwdriver. A trial femoral component 62 which mates substantially precisely with the cuts which have been made in the bone by the use of the cutting block 11 is then applied to the distal extremity of the femur 52. After the femoral osteotomies are completed, a precision osteotomy (bone cut) of the proximal tibia 66 is made in a manner analogous to that described above using appropriate cutting blocks and the lag screws for fixation of the cutting blocks. The remainder of the procedure for a total knee replacement can then follow the conventional procedures which have been utilized in the past with conventional apparatus and/or tools.

From the foregoing it can be seen that there has been provided an apparatus and method which is suitable for achieving a rigid fixation of cutting guides for making precision cuts of the bone. This rigid fixation is obtained by applying compressive forces between the cutting block and the bone. This approach which is used by applicant is simple and does not require complicated or expensive tools or equipment.

Although the present invention has been described in connection with total knee replacements, it should be appreciated that the concept of using compressive forces between a cutting guide and the bone can be useful in other forms of osteotomy, as for example in connection with other joint replacements, such as the elbow, shoulder, hip or ankle.

What is claimed is:

1. An apparatus for making precise cuts in a bone comprising:
a cutting block having a plurality of saw guiding slots and at least one hole extending threrethrough, and hole having a first portion and a second portion with the second portion having a cross sectional area less than that of the first portion so that a seat is formed in the cutting block and a lag screw disposed in said hole in said block and having a cylindrical threaded portion and a head portion, said head portion having a seat portion engaging the seat in the cutting block whereby as said lag screw is threaded into said bone cutting block is secured in a fixed position on said bone.

2. Apparatus as in claim 1 wherein at least certain of said saw guiding slots are inclined at an angle and extend through said hole above said seat so that they clear the head of the lag screw when it is disposed in said hole with its seat portion engaging said seat.

3. Apparatus as in claim 1 wherein said seat is inclined inwardly and downwardly and wherein said seat portion is provided with a downwardly angled peripheral surface.

* * * * *